US00PP32148P2

(12) United States Plant Patent
Kobayashi

(10) Patent No.: US PP32,148 P2
(45) Date of Patent: Sep. 1, 2020

(54) **NEW GUINEA *IMPATIENS* PLANT NAMED 'DONGIMPROLHOPIN'**

(50) Latin Name: *Impatiens hawkeri*
Varietal Denomination: Dongimprolhopin

(71) Applicant: DUMMEN GROUP B.V., De Lier (NL)

(72) Inventor: Ruth Kobayashi, Carlsbad, CA (US)

(73) Assignee: Duümmen Group B.V., De Lier (NL)

( * ) Notice: Subject to any disclaimer, the term of this patent is extended or adjusted under 35 U.S.C. 154(b) by 0 days.

(21) Appl. No.: 16/501,414

(22) Filed: Apr. 9, 2019

(51) Int. Cl.
*A01H 5/02* (2018.01)
*A01H 6/16* (2018.01)

(52) U.S. Cl.
USPC ..... Plt./318.6

(58) Field of Classification Search
USPC ..... Plt./318.6
CPC ..... A01H 5/0261; A01H 5/02; A01H 5/00; A01H 6/16; A01H 6/165; A01H 5/0272
See application file for complete search history.

(56) References Cited

U.S. PATENT DOCUMENTS

PP26,752 P2 * 5/2016 Kientzler ..... A01H 6/16
Plt./318.6

OTHER PUBLICATIONS

Issuu Dummen Orange Bedding Plants Pot Carnations 2018-2019, retrieved on Dec. 3, 2019 [online] retrieved from the Internet at https://issuu.com/bepplersrl/docs/dummen_muskatli_balkon_katalogus_20, 3 cover pages, pp. 1-2, 70, 73, 153. (Year: 2018).*
Upov Pluto Plant Variety Database 20191202, retrieved on Dec. 3, 2019 [online] retrieved from the Internet at https://www.upov.int/pluto/en/index.jsp, one page. (Year: 2019).*

* cited by examiner

*Primary Examiner* — June Hwu
(74) *Attorney, Agent, or Firm* — C. A. Whealy

(57) ABSTRACT

A new and distinct cultivar of *Impatiens* plant named 'Dongimprolhopin' characterized by its compact, upright to outwardly spreading and mounding plant habit; moderately vigorous growth habit; freely branching habit; dark green-colored leaves; freely and early flowering habit; large bright red purple-colored flowers that are undulate; and good garden performance.

2 Drawing Sheets

Botanical designation: *Impatiens hawkeri.*
Cultivar denomination: 'DONGIMPROLHOPIN'.

BACKGROUND OF THE INVENTION

The present invention relates to a new and distinct cultivar of New Guinea *Impatiens* plant, botanically known as *Impatiens hawkeri* and hereinafter referred to by the name 'Dongimprolhopin'.

The new *Impatiens* plant is a product of a planned breeding program conducted by the Inventor in Koka, Ethiopia and Encinitas, Calif. The objective of the breeding program is to create new early and freely flowering New Guinea *Impatiens* plants with large attractive flowers and good garden performance.

The new *Impatiens* plant originated from a cross-pollination made by the Inventor in November, 2015 in Koka, Ethiopia of a proprietary selection of *Impatiens hawkeri* identified as code number NN13-007078-004, not patented, as the female, or seed, parent with *Impatiens hawkeri* 'Kirocolete', disclosed in U.S. Plant Pat. No. 26,752, as the male, or pollen, parent. The new *Impatiens* plant was discovered and selected by the Inventor as a single flowering plant from within the progeny of the stated cross-pollination in a controlled greenhouse environment in Encinitas, Calif. in April, 2016.

Asexual reproduction of the new *Impatiens* plant by terminal vegetative cuttings in a controlled greenhouse environment in Encinitas, Calif. since June, 2016 has shown that the unique features of this new *Impatiens* plant are stable and reproduced true to type in successive generations.

SUMMARY OF THE INVENTION

Plants of the new *Impatiens* have not been observed under all possible combinations of environmental conditions and cultural practices. The phenotype may vary somewhat with variations in environmental conditions such as temperature, daylight and light intensity without, however, any variance in genotype.

The following traits have been repeatedly observed and are determined to be the unique characteristics of 'Dongimprolhopin'. These characteristics in combination distinguish 'Dongimprolhopin' as a new and distinct *Impatiens* plant:

1. Compact, upright to outwardly spreading and mounding plant habit.
2. Moderately vigorous growth habit.
3. Freely branching habit.
4. Dark green-colored leaves.
5. Freely and early flowering habit.
6. Large bright red purple-colored flowers that are undulate.
7. Good garden performance.

Plants of the new *Impatiens* can be compared to plants of the female parent selection. Plants of the new *Impatiens* differ primarily from plants of the female parent selection in the following characteristics:

1. Plants of the new *Impatiens* are more compact than and not as vigorous as plants of the female parent selection.
2. Flowers of plants of the new *Impatiens* are bright red purple in color whereas flowers of plants of the female parent selection are dark lavender pink in color.

Plants of the new *Impatiens* can be compared to plants of 'Kirocolete'. Plants of the new *Impatiens* differ primarily from plants of 'Kirocolete' in the following characteristics:

1. Petal margins of plants of the new *Impatiens* are more frilled than petal margins of plants of 'Kirocolete'.
2. Flowers of plants of the new *Impatiens* are bright red purple in color whereas flowers of plants of 'Kirocolete' are bright fuchsia in color.

Plants of the new *Impatiens* can be compared to plants of *Impatiens hawkeri* 'Doimmalaven', disclosed in U.S. Plant Pat. No. 30,744. In side-by-side comparisons, plants of the new *Impatiens* differ primarily from plants of 'Doimmalaven' in the following characteristics:

1. Plants of the new *Impatiens* are more compact than and not as vigorous as plants of 'Doimmalaven'.
2. Plants of the new *Impatiens* have smaller flowers than plants of 'Doimmalaven'.
3. Flowers of plants of the new *Impatiens* are undulate with frilled petal margins whereas flowers of plants of 'Doimmalaven' are mostly flat and have entire margins.
4. Flowers of plants of the new *Impatiens* are bright red purple in color whereas flowers of plants of 'Doimmalaven' are purple to red purple in color.

Plants of the new *Impatiens* can be compared to plants of *Impatiens hawkeri* 'Kironanete', disclosed in U.S. Plant Pat. No. 26,753. In side-by-side comparisons, plants of the new *Impatiens* differ primarily from plants of 'Kironanete' in the following characteristics:

1. Plants of the new *Impatiens* are more compact than and not as vigorous as plants of 'Kironanete'.
2. Plants of the new *Impatiens* have larger flowers than plants of 'Kironanete'.
3. Petal margins of plants of the new *Impatiens* are more frilled than petal margins of plants of 'Kironanete'.
4. Flowers of plants of the new *Impatiens* are bright red purple in color whereas flowers of plants of 'Kironanete' are dark cherry red in color.

BRIEF DESCRIPTION OF THE PHOTOGRAPHS

The accompanying colored photographs illustrate the overall appearance of the new *Impatiens* plant showing the colors as true as it is reasonably possible to obtain in colored reproductions of this type. Colors in the photographs may differ slightly from the color values cited in the detailed botanical description which accurately describe the colors of the new *Impatiens* plant.

The photograph on the first sheet is a side perspective view of a typical flowering plant of 'Dongimprolhopin' grown in a container.

The photograph on the second sheet is a close-up view of a typical flowering plant of 'Dongimprolhopin'.

DETAILED BOTANICAL DESCRIPTION

The aforementioned photographs and following observations, measurements and values describe plants grown during the winter and early spring in 15.25-cm containers in a polyethylene-covered greenhouse in Encinitas, Calif. and under cultural practices typical of commercial New Guinea *Impatiens* production. During the production of the plants, day temperatures averaged 25° C., night temperatures averaged 20° C. and light levels ranged from 4,000 to 4,500 lux. Plants were 16 weeks old when the photographs and description were taken. In the following description, color references are made to The Royal Horticultural Society Colour Chart, 2015 Edition, except where general terms of ordinary dictionary significance are used.

Botanical classification: *Impatiens hawkeri* 'Dongimprolhopin'.

Parentage:

*Female, or seed, parent.*—Proprietary selection of *Impatiens hawkeri* identified as code number NN13-007078-004, not patented.

*Male, or pollen, parent.*—*Impatiens hawkeri* 'Kirocolete', disclosed in U.S. Plant Pat. No. 26,752.

Propagation:

*Type.*—By terminal vegetative cuttings.

*Time to initiate roots, summer and winter.*—About five to seven days at temperatures about 20° C.

*Time to produce a rooted young plant, summer and winter.*—About three weeks at temperatures about 20° C.

*Root description.*—Fine, fibrous; typically white in color, actual color of the roots is dependent on substrate composition, water quality, fertilizers, substrate temperature and age of roots.

*Rooting habit.*—Freely branching; dense.

Plant description:

*Plant and growth habit.*—Compact, upright to outwardly spreading and mounding plant habit; broad inverted triangle in overall shape; freely branching habit with lateral branches potentially developing at every node; moderately vigorous growth habit and moderate growth rate.

*Plant height.*—About 27 cm.

*Plant diameter.*—About 53 cm.

Lateral branch description:

*Length.*—About 24.5 cm.

*Diameter.*—About 1.1 cm.

*Internode length.*—About 4.1 cm.

*Strength.*—Strong, flexible.

*Aspect.*—Initially upright to outwardly spreading.

*Texture and luster.*—Smooth, glabrous; glossy.

*Color, developing.*—Close to between 177A and 178A.

*Color, fully developed.*—Close to 146A variably tinged with close to 178A and 183A.

Leaf description:

*Arrangement.*—Typically in whorls; simple.

*Length.*—About 12.5 cm.

*Width.*—About 4.5 cm.

*Shape.*—Lanceolate.

*Apex.*—Acuminate.

*Base.*—Cuneate.

*Margin.*—Serrate with ciliation.

*Texture and luster, upper surface.*—Smooth, glabrous; glossy.

*Texture and luster, lower surface.*—Smooth, glabrous; somewhat glossy.

*Venation pattern.*—Pinnate; arcuate.

*Color.*—Developing leaves, upper surface: Close to NN137A. Developing leaves, lower surface: Close to 138A. Fully expanded leaves, upper surface: Darker green than N189A; venation, close to 145C. Fully expanded leaves, lower surface: Close to 191A; venation, close to 53B to 53C.

*Petiole length*.—About 5 cm.

*Petiole diameter*.—About 5 mm.

*Petiole texture and luster, upper and lower surfaces*.—Smooth, glabrous; somewhat glossy.

*Petiole color, upper surface*.—Close to 145B to 145C.

*Petiole color, lower surface*.—Close to 145B to 145C variably tinged with 53B to 53C.

Flower description:

*Flower type and flowering habit*.—Single oval to rounded axillary flowers that are undulate; freely flowering habit, typically about eight to ten open flowers and flower buds per lateral branch; flowers positioned above and beyond the foliar plane, flowers typically face mostly upright to outwardly.

*Flower longevity*.—Flowers typically last about four to seven days on the plant under greenhouse conditions; petals self-cleaning, gynoecium persistent.

*Fragrance*.—None detected.

*Natural flowering season*.—Year-round under greenhouse conditions; in the garden, flowering from spring until fall in California; early flowering habit, plants typically begin flowering about ten weeks after planting.

*Flower buds*.—Length: About 2 cm. Diameter: About 1 cm. Shape: Ovoid; flower buds opening "rose-like". Texture and luster: Smooth, glabrous; matte. Color: Petals, close to 68A; sepals, close to 146B.

*Flower diameter*.—About 6.75 cm by 6.25 cm.

*Flower depth*.—About 1.5 cm.

*Petals*.—Quantity and arrangement: Five per flower in a single whorl. Length, banner petal: About 3.5 cm. Length, lateral petals: About 3 cm. Length, lower petals: About 3.5 cm. Width, banner petal: About 5.5 cm. Width, lateral petals: About 4.2 cm. Width, lower petals: About 4.75 cm. Shape, all petals: Broadly cordate. Apex, all petals: Cordate to rounded. Base, all petals: Obtuse. Margin, all petals: Scalloped; moderately undulate and frilled, ruffled appearance. Texture and luster, all petals, upper surface: Smooth, glabrous; velvety; matte. Texture and luster, all petals, lower surface: Smooth, glabrous; matte. Color, banner and lower petals: When opening and fully opened, upper surface: More intense than between N57A and N66A; towards the base, close to N57C; venation, similar to lamina; color does not change with development. When opening and fully opened, lower surface: Close to N57C; towards the base, close to N570; venation, similar to lamina; color towards the base becoming closer to N57D to lighter than N57D with development. Color, lateral petals: When opening and fully opened, upper surface: More intense than between N57A and N66A; towards the base, close to N57A; venation, similar to lamina; color becoming closer to N66B and towards the base becoming closer to N57D to lighter than N57D with development. When opening and fully opened, lower surface: Close to N57C; towards the base, close to N57D; venation, similar to lamina; color does not change with development.

*Sepals*.—Quantity and arrangement: Three in a single whorl; one modified into an elongated spur; curvature of the spur is medium. Lateral sepal length: About 1 cm. Lateral sepal width: About 7 mm. Lateral sepal shape: Elongated deltoid. Lateral sepal apex: Cuspidate. Lateral sepal base: Truncate. Lateral sepal margin: Entire. Lateral sepal texture and luster, upper and lower surfaces: Smooth, glabrous; matte. Lateral sepal color, upper surface: Close to 145A. Lateral sepal color, lower surface: Close to 146A. Spur length: About 3.5 cm. Spur diameter: At flower, about 3 mm; at apex, about 1 mm. Spur texture and luster: Smooth, glabrous; somewhat glossy. Spur color: Close to 53C.

*Peduncles*.—Length: About 5 cm. Diameter: About 2.75 mm. Angle: About 45° from vertical. Strength: Strong; flexible. Texture and luster: Smooth, glabrous; slightly glossy. Color: Close to 146A to 146B variably tinged with close to 178A and 183A.

*Reproductive organs*.—Stamens: Quantity: Five fused at anthers; filaments free. Anther size: About 6 mm by 2 mm. Anther shape: Oblong. Anther color: Close to 11D; proximally, close to N57A. Pollen amount: Moderate. Pollen color: Close to 10D. Pistils: Quantity per flower: One. Pistil length: About 6 mm. Stigma shape: Crested. Stigma color: Close to 144A. Style color: Close to 144A. Ovary color: Close to 144A.

*Seeds and fruits*.—To date, seed and fruit production has not been observed on plants of the new *Impatiens*.

Pathogen & pest resistance: To date, plants of the new *Impatiens* have not been observed to be resistant to pathogens and pests common to *Impatiens* plants.

Garden performance: Plants of the new *Impatiens* have been observed to have good garden performance and tolerate temperatures ranging from about 5° C. to about 40° C.

It is claimed:

1. A new and distinct *Impatiens* plant named 'Dongimprolhopin' as illustrated and described.

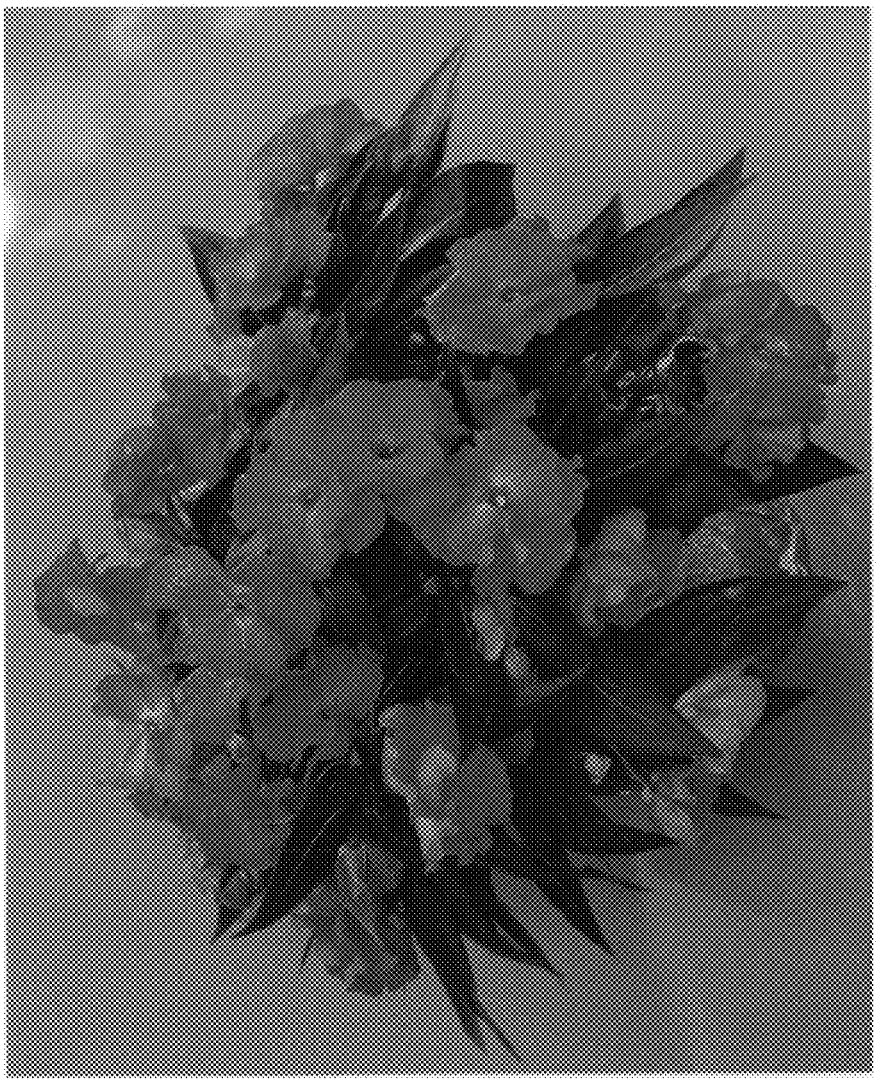

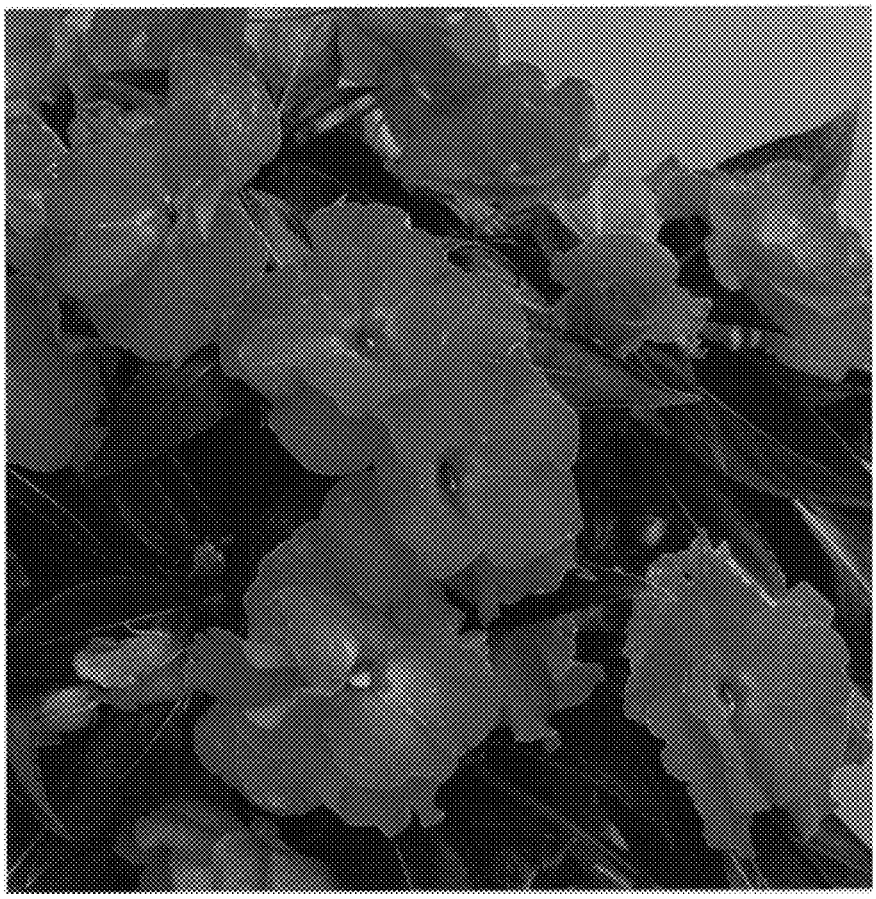

* * * * *